United States Patent [19]
Carmody et al.

[11] Patent Number: 5,482,600
[45] Date of Patent: Jan. 9, 1996

[54] PROCESS TO IMPROVE COLOR IN ANTIPERSPIRANT SOLUTIONS

[75] Inventors: Walter J. Carmody, Port Jervis; Gary J. Coleman, Deerpark Township, Orange County, both of N.Y.

[73] Assignee: Somerville Technology Group, Inc., Huguenot, N.Y.

[21] Appl. No.: 258,430

[22] Filed: Jun. 10, 1994

[51] Int. Cl.[6] .............................. A61K 7/34; A61K 7/36; A61K 7/38; B01D 5/00
[52] U.S. Cl. ..................... 204/157.15; 424/59; 424/66; 424/67; 424/68
[58] Field of Search ................. 424/59, 66, 67, 424/68; 204/157.14, 157.15

[56] References Cited

U.S. PATENT DOCUMENTS

| | | | |
|---|---|---|---|
| 3,025,220 | 3/1962 | Kunz et al. | 204/157.15 |
| 3,112,252 | 11/1963 | Stoops et al. | 204/157.15 |
| 3,346,474 | 10/1967 | Gush | 204/157.15 |
| 4,980,038 | 12/1990 | Watanabe et al. | 204/157.15 |

FOREIGN PATENT DOCUMENTS

| | | | |
|---|---|---|---|
| 2842691 | 4/1980 | Germany | 204/157.14 |
| 459477 | 3/1975 | U.S.S.R. | 204/157.15 |

Primary Examiner—Dale R. Ore
Attorney, Agent, or Firm—Kenneth P. Glynn

[57] ABSTRACT

The present invention process involves the exposure of antiperspirant salt solutions to ultraviolet light to cause lightening in color. The ultraviolet light can be in the wavelength range of 180 to 400 nanometers, with the longer wavelengths preferred and at an exposure time of 1 to 120 minutes. The color of the antiperspirant solutions treated with ultraviolet light approaches the color of water, commonly known in the cosmetic industry as water white. These exceptionally low color antiperspirant salt solutions are useful in development of clear and colorless antiperspirant gels, roll-ons and stick formulations.

8 Claims, 1 Drawing Sheet

5,482,600

PROCESS TO IMPROVE COLOR IN ANTIPERSPIRANT SOLUTIONS

BACKGROUND OF THE INVENTION

1. Field of the Invention

The present invention relates to a process for improving color in antiperspirant solutions by treatment with specified wavelength ultraviolet light for specified times to approach and/or achieve water white color.

2. Information Disclosure Statement

Previous attempts to maintain or improve whiteness (clarity) in antiperspirant solutions have involved various technical attempts to minimize iron content either in the procurement of pre-reaction components in the processing of end products themselves. However, none of the prior art methods involved the use of selected wavelength ultraviolet light for specified times to approach and/or achieve water white color.

SUMMARY OF THE INVENTION

The present invention is a process for improving color in antiperspirant solutions. It has been discovered that exposure to ultraviolet light causes antiperspirant salt solutions to lighten in color. Antiperspirant solutions are treated with Ultraviolet Light in the wavelength range of 180 to 400 nanometers, with the longer wavelengths of that range preferred, and at an exposure time of 1 to 120 minutes. The antiperspirant salts treated by this method include all generally recognized classes of antiperspirant salts including aluminum chlorohydrate, aluminum sesquichlorohydrate, aluminum zirconium trichlorohydrex-glycine and aluminum zirconium tetrachlorohydrex-glycine. Antiperspirant solutions can be prepared using solvents such as, but not exclusively water, hydroxylated organics including propylene glycol, dipropylene glycol, polyethylene glycol, propylene carbonate, and mixtures of the above solvents as well as other common hydrophilic solvents. The color of the antiperspirant solutions treated in the present invention with ultraviolet light approaches the color of water, commonly known in the cosmetic industry as water white. The resulting exceptionally low color antiperspirant salt solutions are useful in development of clear and colorless antiperspirant gels, roll-ons and stick formulations.

BRIEF DESCRIPTION OF THE DRAWINGS

The present invention is more fully understood when the specification herein is taken in conjunction with the drawings appended hereto, wherein.

DETAILED DESCRIPTION OF THE PRESENT INVENTION

Figure 1:
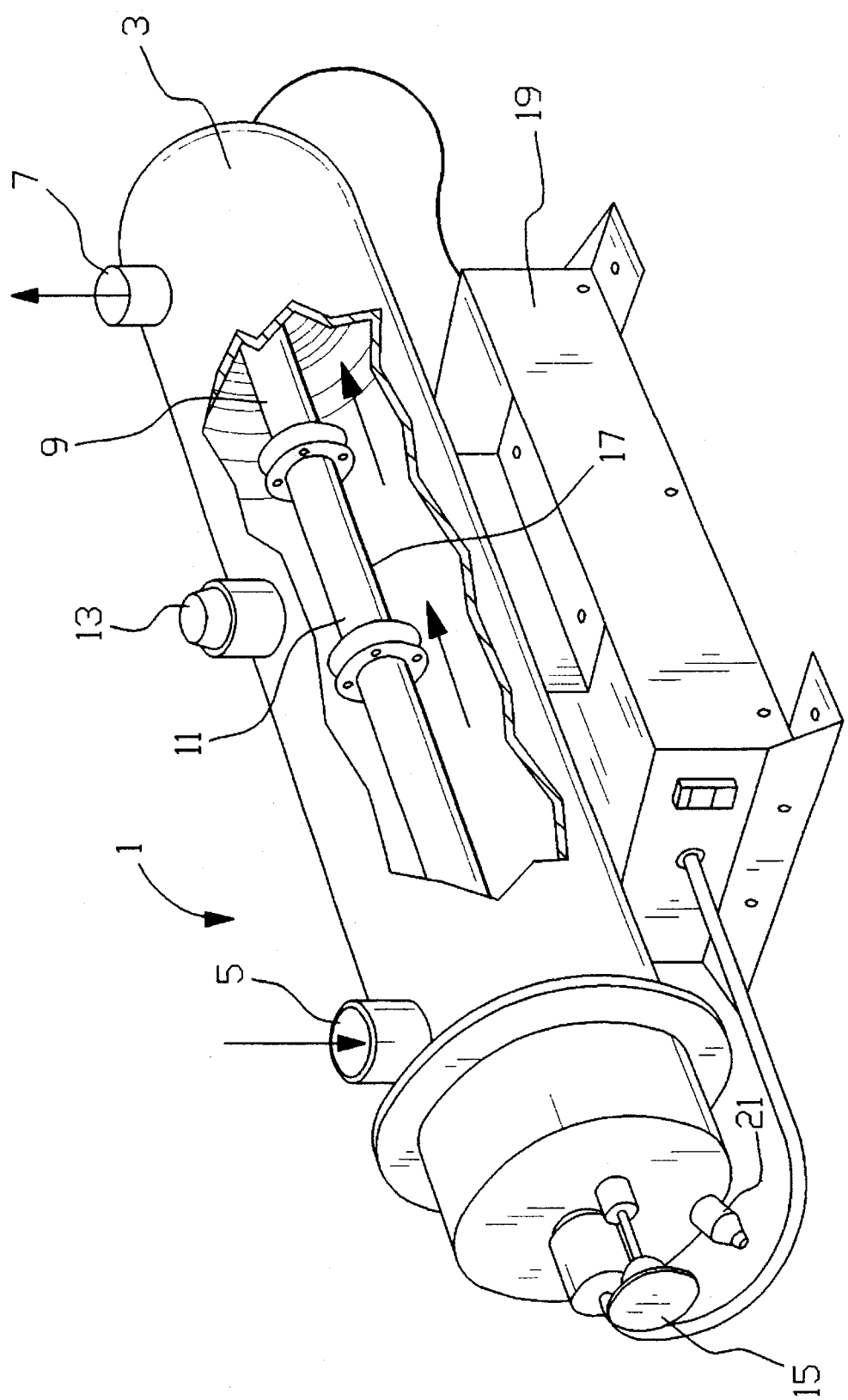
FIG. 1 shows a device for treating antiperspirant solutions by the process of the present invention.

The antiperspirant industry has always been concerned with the color of the antiperspirant salts used to reduce underarm wetness. Antiperspirant salts in solution or powder form tend to be off-white to yellow in color. The color can be attributed to metallic cations such as aluminum, zirconium and or traces of iron reacting with each other and with the antiperspirant anionic components such as chloride. It has always been the goal to minimize the color of antiperspirant salts with the color being dependent on the antiperspirant category or salt empirical composition.

In antiperspirant solution form, where water or propylene glycol are the predominant solvents, the color is critical because off white or yellow antiperspirant salts have a consumer perception as being un-natural or dirty. Low color or water white, the color of water, antiperspirant solutions are very useful in the development of clear and colorless antiperspirant formulations which have a very desirable appeal to the consumer.

It has been found that exposing antiperspirant salts to intense ultraviolet light causes the salts to lighten in color. These antiperspirant salts include aluminum chlorohydrate, aluminum sesquichlorohydrate, aluminum zirconium trichlorohydrex-glycine and aluminum zirconium tetrachlorohydrex-glycine. Antiperspirant solutions can be prepared using solvents such as, but not exclusively water, hydroxylated organics including propylene glycol, dipropylene glycol, polyethylene glycol, propylene carbonate, and mixtures of the above solvents as well as other common hydrophilic solvents. The yellow color of an antiperspirant solution can be eliminated or substantially reduced by the use of ultraviolet light. The resulting solution, very clear and colorless, is very useful in formulating clear antiperspirant products.

The final color of a given antiperspirant solution is dependent on the chemical composition, and concentration of the solution as well as ultraviolet light wavelength, intensity, and duration of exposure.

In the process of the present invention, the antiperspirant solution may be exposed to ultraviolet rays either in batch process or in a continuous process. FIG. 1 shows a piece of equipment shown generally as device 1. This includes a main chamber 3 with an inlet 5 for continuous flow of antiperspirant solutions and an outlet 7, as shown. Antiperspirant solutions flow around ultraviolet light generator 11. There is a sight port 13, a wiper knob 15 and a wiper rod 17, along with a transformer housing and junction box 19. There is also provided a drain 21 as shown.

In the process of the present invention, the ultraviolet light is utilized in a range of 180 to 400 nanometers, and preferably about 325 to 400 nanometers. The ultraviolet light is generally utilized with an intensity appropriate with the holding time and color of the particular antiperspirant solution. Factor holding or exposure times require greater intensities. Holding times may range from as low as one minute to as much as two hours or longer but as a practical matter for commercial productions, exposure times of under one hour are desirable and are successful. Very good results may be achieved with only one half hour of exposure. While the wattage may vary, as mentioned, depending upon exposure time and the solution, intensities as low as 300 watts and as high as 1000 watts may be used.

The following example illustrates the invention.

EXAMPLE I 900 grams of an aluminum zirconium Tetrachlorohydrex-glycine, AZG propylene glycol 45 percent concentration solution, nominal formula; $Al_{3.6} Zr(OH)_{11.6} Cl_{3.2} \times nH_2O$, lot number 004-07 was placed in an open Pyrex pan resulting in a one inch layer of solution. The pan, containing the AZG propylene glycol solution was placed 12 inches below an ultraviolet A lamp. The lamp unit, a "UVA 400" supplied by Unified Technologies of East Hartford, Conn. contains a one inch arc length mercury vapor lamp with an ultraviolet output maximum at 365 nanometers and rated at 450 watts. The AZG propylene glycol solution was exposed to the ultraviolet, UVA light for 45 minutes. The liquid, before and after exposure to the UV light was tested for color, using the color test method described in attachment 1. The results, Table I clearly shows a drop in color, approaching water white, after exposure to UVA light.

The test was repeated using fresh AZG propylene glycol solution that had not previously been exposed to UVA light with the solution at ¼ inch depth in the pan. The sample was similarly placed 12 inches below the UVA light and exposed for 45 and 60 minutes. This solution was tested for color using the same test method as described in attachment 1. Results are summarized in Table I.

TABLE I

| Sample | Description | Color |
| --- | --- | --- |
| Deionized water | no UVA exposure | 2.2 |
| AZG PG solution | control, no UVA exposure | 6.2 |
| AZG PG solution | 1 inch deep, 45 min. exposure | 3.4 |
| AZG PG solution | ¼ inch deep, 45 min. exposure | 2.4 |
| AZG PG solution | ¼ inch deep, 60 min. exposure | 2.3 |

EXAMPLE II

Using a freshly prepared 45 percent concentration AZG propylene glycol solution, lot number 004-10 a ½ inch layer was placed in a Pyrex pan. The pan, with the AZG propylene glycol solution was placed 12 inches under the UVA described in Example I. An initial sample was taken prior to exposure to the UVA light and used as a control sample. The lamp was turned on and allowed to warm up for two minutes. The liquid was exposed to the UVA light for a total of 120 minutes with samples taken every 15 minutes starting at 30 minutes. The results, Table II shows a steady decrease in color with exposure to UVA light.

TABLE II

| Sample/Description | Color |
| --- | --- |
| Initial, no exposure | 8.5 |
| 30 minutes exposure | 6.6 |
| 45 minutes exposure | 5.6 |
| 60 minutes exposure | 5.1 |
| 90 minutes exposure | 4.8 |
| 120 minutes exposure | 4.7 |

EXAMPLE III

A sample of an AZG propylene glycol solution, lot number 004-09 was placed in a Pyrex pan in four trial runs so that four different depths were obtained; ¼, ½, ¾ and one inch. Each trail run sample was placed seven inches below a UVA lamp, described in Example I and exposed to UVA light for 45 minutes. Samples of each trial were taken prior to exposure to UVA light and after 15, 30, and 45 minutes of exposure. Every sample was then tested for color using the color test method, attachment 1. The results are reported in Table III.

TABLE III

| Sample/Description | Color |
| --- | --- |
| ¼ inch deep | |
| initial, control sample no UVA exposure | 6.7 |
| 15 minutes exposure | 4.2 |
| 30 minutes exposure | 3.4 |
| 45 minutes exposure | 3.3 |
| ½ inch deep | |
| 15 minutes exposure | 4.4 |
| 30 minutes exposure | 3.4 |
| 45 minutes exposure | 3.4 |
| ¾ inch deep | |
| 15 minutes exposure | 5.0 |
| 30 minutes exposure | 3.7 |
| 45 minutes exposure | 3.6 |
| 1 inch deep | |
| 15 minutes exposure | 5.6 |
| 30 minutes exposure | 4.4 |
| 45 minutes exposure | 4.4 |

EXAMPLE IV

An aqueous antiperspirant solution was prepared in the following way; a 50 percent concentration aluminum chlorohydrate, ⅚ basic, aqueous solution, ACH, nominal formula; $Al_2 (OH)_5 Cl{\times}nH_2O$ was mixed with a 40 percent concentration zirconyl hydroxy chloride glycine aqueous solution producing an aluminum zirconium tetrachlorohydrex-glycine, AZG aqueous solution. Ultraviolet, UVA light was used to expose two liquid portions; the zirconyl hydroxy chloride glycine solution and the AZG solution where the zirconyl hydroxy chloride glycine solution was combined with the aluminum chlorohydrate solution prior to exposure to UVA light.

A zirconyl hydroxy chloride glycine solution, 40 percent concentration known as Part A was prepared and filtered. This solution was added to a Pyrex pan to a depth of one inch. The pan, containing the solution was placed ten inches below a UVA lamp, described in Example I. The solution was exposed to UVA light for 30 minutes. The solution was then removed from under the light and combined with an appropriate amount of ACH liquid to produce an AZG solution where the aluminum:zirconium mole ratio was 3.6:1. The color of the AZG solution was determined.

An AZG solution was prepared by combining a freshly prepared 40 percent concentration Part A aqueous solution and a 50 percent concentration ACH liquid so that the final, AZG aqueous solution had an aluminum:zirconium mole ratio of 3.6:1. This AZG solution was placed in a Pyrex pan to a depth of one inch. The pan, containing the AZG solution was placed 10 inches under the UVA lamp and the liquid was exposed to the UVA light for 30 minutes. The liquid was removed from under the light and tested for color. A sample of this liquid was tested for color before exposure to UVA light. Results are found in Table IV.

TABLE IV

| Sample/Description | Color |
| --- | --- |
| Control, AZG aq. solution, no UV light exposure | 2.6 |
| AZG aq. solution, Part A exposed to UV light | 2.2 |
| AZG aq. solution, AZG solution exposed to UV light | 2.5 |

EXAMPLE V

A 45 percent concentration AZG propylene glycol solution, lot number 004-08 was placed in a Pyrex pan to a depth of one inch. The pan, with the AZG propylene glycol solution was placed 12 inches below the UVA lamp described in Example I. The solution was exposed to UVA light for 30 minutes then removed and tested for color. The UVA exposed liquid was then placed in a round bottom flask fitted with a thermometer, water cooled condenser and glass stir rod. While stirring, the liquid was heated to 90° C. and held for 6 hours. The liquid was then removed from the flask, cooled to room temperature and tested for color. The results are in Table V.

TABLE V

| Sample/Description | Color |
| --- | --- |
| Control, AZG PG solution, no UVA light exposure | 7.0 |
| AZG PG solution, 30 minutes exposure | 2.8 |
| AZG PG solution, 30 min. exposure, then 6 hours at 90 C. | 2.7 |

EXAMPLE VI

Ten gallons of a zirconyl hydroxy chloride glycine aqueous solution, Part A, was prepared. The liquid was split in three portions for UV testing with a small amount set aside as a control, un-exposed sample.

One portion of the zirconyl hydroxy chloride glycine solution was passed through a Sanitron Ultraviolet Water Purifier, model number S37A, supplied by Atlantic Ultraviolet Corporation, Bay Shore, N.Y., Diagram 1. The unit was fitted with a mercury vapor lamp with a maximum ultraviolet light output at 254 nanometers. The flow rate for this one pass trial was determined to be 4.5 gallons per hour. After four gallons had passed through the unit, a sample was collected and tested for color.

Another portion of the same zirconyl hydroxy chloride glycine solution was continuously recycled through the above UV unit for three hours. The flow rate was set at 62 gallons per hour. Samples of the solution were taken at specific intervals and the color determined.

The third portion of the same liquid was placed in a Pyrex pan to a depth of one inch and placed ten inches below a UV A lamp, as described in Example I. The solution was exposed to the UVA light under static conditions with samples taken at 15 and 30 minutes then tested. The results of the above trials are in Table VI.

TABLE VI

| Sample/Description | Color |
| --- | --- |
| Control, Part A no UV light | 2.6 |
| Part A, 1 pass thru system | 2.2 |
| Part A, multi pass thru system | |
| ½ hour | 2.4 |
| 1 hour | 2.4 |
| 2 hours | 2.3 |
| 2.5 hours | 2.3 |
| 3 hours | 2.3 |
| Part A under UVA lamp, static conditions | |
| 15 minutes | 2.3 |
| 30 minutes | 2.2 |

EXAMPLE VII

Aluminum chlorohydrate, ACH was dissolved in propylene glycol to produce a 40 percent concentration solution. A one inch deep layer of this liquid was placed in a Pyrex pan and then placed under the UV A lamp described in Example I. The solution was exposed to UV A light for twenty minutes. The color of the initial and UV A exposed liquid was determined and listed in Table VII.

EXAMPLE VIII 360 grams of aluminum sesquichlorohydrate, with a typical formula of $Al_2$ $(OH)_{4.5}$ $Cl_{1.5} \times nH_2O$ was dissolved in propylene glycol to produce a 40 percent concentration solution. This solution was similarly treated, by exposure to UV A light, as the ACH propylene glycol solution in Example VII. The color of the liquid was determined before and after exposure to UV A light. Results are listed in Table VII.

EXAMPLE IX

A 40 percent concentration of aluminum zirconium trichlorohydrex-gly propylene glycol solution with a nominal formula of $Al_{3.3}$ $Zr(OH)_{11.3}$ $Cl_{2.6} \times nH_2O$—glycine was prepared. A one inch layer of this solution was placed in a glass pan and then placed under the UVA lamp as described in Example I. The solution was exposed to the UVA light for 20 minutes. The color of the solution was determined before and after exposure. The results are in Table VII.

TABLE VII

| Sample/Description | Color |
| --- | --- |
| ACH PG solution control, no UV exposure | 6.8 |
| ACH PG solution UV exposed | 3.7 |
| Aluminum Sesquichlorohydrate PG control | 6.1 |
| Aluminum Sesquichlorohydrate PG UV exposed | 2.8 |
| Aluminum Zirconium Trichlorohydrex-gly PG solution, control | 5.6 |
| Aluminum Zirconium Trichlorohydrex-gly PG solution, UV exposed | 4.2 |

EXAMPLE X

An AZG propylene glycol, 30 percent concentration solution, lot number 004-16 was formulated and split into two portions. One portion of the AZG propylene glycol solution was added to a glass pan so that a one inch layer resulted. The pan, with the AZG propylene glycol solution was placed four inches below a UVA lamp unit. The lamp unit was a Porta Cure 1000, five inch arch length, 200 watts per inch, maximum wavelength output at 365 nanometers and supplied by American Ultraviolet Company of Murray Hill, N.J. The solution was exposed to the UVA light after a five minute lamp warm up. Samples were taken at zero, one, three and five minute intervals and their color determined.

The above test was repeated with the second portion of the AZG solution where the liquid was placed 12 inches below the UVA lamp unit described above. Samples were taken at zero, one, two, three, four, six, eight and ten minutes of exposure and tested for color. Results from both tests are in Table VIII.

TABLE VIII

| Sample/Description | Color |
| --- | --- |
| AZG PG solution, 4 inch distance | |
| 0 minute exposure | 5.1 |
| 1 minute exposure | 4.6 |
| 3 minute exposure | 3.1 |
| 5 minute exposure | 2.8 |
| AZG PG solution, 12 inch distance | |
| 0 minute exposure | 5.1 |
| 1 minute exposure | 4.9 |
| 2 minute exposure | 4.7 |
| 3 minute exposure | 4.4 |
| 4 minute exposure | 4.6 |
| 6 minute exposure | 4.3 |
| 8 minute exposure | 3.5 |
| 10 minute exposure | 3.2 |

Obviously, numerous modifications and variations of the present invention are possible in light of the above teachings. It is therefore understood that within the scope of the appended claims, the invention may be practiced otherwise than as specifically described herein.

What is claimed is:

1. A process for reducing color and increasing clearness in an antiperspirant solution, which comprises:

treating said solution with ultraviolet light in the wavelength range of about 180 to about 400 nanometers for an exposure time of at least about one minute.

2. The process of claim 1 wherein said exposure time is about one minute to about 120 minutes.

3. The process of claim wherein said wavelength range is about 325 to about 400 nanometers.

4. The process of claim 2 wherein said wavelength range is about 325 to about 400 nanometers.

5. The process of claim 1 wherein said antiperspirant solution contains at least one salt selected from the group consisting of aluminum chlorohydrate, aluminum sesquichlorohydrate, aluminum zirconium trichlorohydrex-glycine, aluminum zirconium tetrachlorohydrex-glycine, aluminum zirconium pentachlorohydrex-gly, and aluminum zirconium octachlorohydrex-gly.

6. The process of claim 5 wherein said at least one salt is in solution with hydroxylate organic solvent.

7. The process of claim 5 wherein said at least one salt is in solution with water.

8. The process of claim 5 wherein said at least one salt is in solution with a hyrdophillic solvent.

* * * * *